United States Patent
Yukimune et al.

(12)

(10) Patent No.: US 6,465,221 B1
(45) Date of Patent: *Oct. 15, 2002

(54) METHOD OF PRODUCING A TAXANE-TYPE DITERPENE

(75) Inventors: Yukihito Yukimune; Yasuhiro Hara; Hiroaki Tan; Ikuo Tomino, all of Yamaguchi (JP)

(73) Assignee: Mitsui Chemicals, Inc., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 14 days.

(21) Appl. No.: 08/562,517

(22) Filed: Mar. 19, 2001

(30) Foreign Application Priority Data

Nov. 25, 1994 (JP) .............................. 6-291783
Dec. 5, 1994 (JP) .............................. 6-301179
Dec. 15, 1994 (JP) .............................. 6-312258
Aug. 28, 1995 (JP) .............................. 7-218874

(51) Int. Cl.[7] .............................................. C12P 17/02
(52) U.S. Cl. ............. 435/123; 435/240.48; 435/240.46; 435/240.4; 435/244; 549/510
(58) Field of Search ........................... 435/123, 240.48, 435/244, 240.46, 240.4; 549/510

(56) References Cited

U.S. PATENT DOCUMENTS 5,019,504 A    5/1991 Christen et al.
5,407,816 A *  4/1995 Bringi et al. ................ 435/123
5,637,484 A    6/1997 Yukimune et al.

FOREIGN PATENT DOCUMENTS

| DE | 4122208 | | 7/1992 |
| EP | 194554 | * | 9/1986 |
| EP | 0521435 | | 1/1993 |
| EP | 0683232 | | 11/1995 |
| WO | 9317121 | | 9/1993 |

OTHER PUBLICATIONS

"Development of callus and cell suspension cultures for taxol production" E.R.M. Wickremesinhe et al., 1992 World Congress on Cell and Tissue Culture.

E.W. Weiler et al., *FEBS Letters,* vol. 345, No. 1, pp. 9–13, (May, 1994).

* cited by examiner

*Primary Examiner*—Irene Marx
(74) *Attorney, Agent, or Firm*—Birch, Stewart, Kolasch & Birch, LLP

(57) ABSTRACT

The present invention relates to a method of producing a taxane-type diterpene wherein a cell and/or a tissue of a plant which produces the taxane-type diterpene is cultured in the presence of at least one substance selected from the group consisting of coronatines, a bacterium which produces the coronatines, a culture solution or a culture extract of such bacterium, cyclic polysaccharides, fatty acids, and an imino or amino derivative of jasmonic acids, then the taxane-type diterpene is recovered from the resulting cultures.

3 Claims, No Drawings

METHOD OF PRODUCING A TAXANE-TYPE DITERPENE

BACKGROUND OF THE INVENTION

1. Field of the Invention

The present invention relates to a method of producing a taxane-type diterpene including taxol which is useful as a therapeutic agent for ovarian cancer, mammary cancer, lung cancer and the like.

2. Description of the Prior Art

Taxol, which is useful as a therapeutic agent for ovarian cancer, mammary cancer, lung cancer and the like, is a taxane-type diterpene identified after being isolated from *Taxus brevifolia* NUTT, which is a plant belonging to genus Taxus, family Taxaceae and has a complex ester group which is related to the above-mentioned pharmacological activity. Taxol can be found in all the parts of the plant body of Taxus brevifolia NUTT, but the bark has been reported to exceed all others in its content of the taxol. At present, taxol is collected from a natural or a cultivated plant body, however, the plant belonging to genus Taxus grows slowly, and it takes more than 10 years to grow to a height of 20 cm above the ground, besides the tree dies after its bark is taken off, thus it has not been easy to obtain a large amount of taxol. It would be advantageous if a taxane-type diterpene such as taxol and/or baccatin III which is a precursor of taxol, can be synthesized by the use of tissue culture, since a large amount of taxol can be easily obtained without cutting down the trees.

As a conventional method of producing taxol by utilizing cultured plant cells, a US patent was issued on a production method utilizing cultured cells of *Taxus brevifolia* NUTT (U.S. Pat. No. 5,019,504), however, the amount of taxol production described therein is 1–3 mg/l, and that is insufficient for the industrial production. Besides, the production of taxol by the cell culture utilizing the conventional tissue culture technique is unstable and even when a primary cell of high productivity can be obtained by selection, it is difficult to keep its content by subculturing [E. R. M. Wickremesine et al., World Congress on Cell and Tissue Culture (1992)].

On the other hand, as a prior art in the taxol production, a semisynthetic method from baccatin III, which is a precursor in biosynthesis of taxol, is disclosed in the specification of U.S. Pat. No. 5,015,744 issued to Holton et al. By the use of the plant tissue culture, a raw material for the semisynthetic process such as baccatin III can be produced, thus the plant tissue culture can be also utilized for taxol production by the above-mentioned semisynthetic process.

OBJECTS AND SUMMARY OF THE INVENTION

The object of the present invention is to provide a simple method of producing a taxane-type diterpene by plant tissue culture.

As a result of the intensive study, the present inventors found that the productivity of the taxane-type diterpene in the cultures can be improved by carrying out the culture of a cultured cell or a cultured tissue of a plant which produces the taxane-type diterpene, in the presence of coronatines, a bacterium which produces the coronatines, a culture solution or a culture extract of such bacteria, cyclic polysaccharides, fatty acids or an imino or amino derivative of jasmonic acids, and completed the present invention.

Accordingly the present invention is a method of producing a taxane-type diterpene wherein a cell and/or a tissue of a plant which produces a taxane-type diterpene is cultured in the presence of at least one substance selected from the group consisting of coronatines, a bacterium which produces the coronatines, a culture solution or a culture extract of such bacterium, cyclic polysaccharides, fatty acids, and a compound represented by the general formula (X):

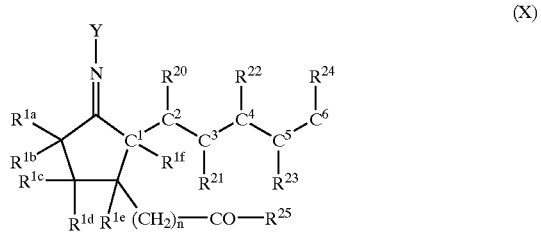

[wherein,

Y is hydrogen atom, hydroxyl group, cyano group, $NR^{28a}R^{28b}$ (wherein $R^{28a}$ and $R^{28b}$ independently represent hydrogen atom, carbamoyl group, acyl group having 1 to 12 carbon atoms, alkyl group having 1 to 12 carbon atoms, aryl group, aryl group having a substituent, arylalkyl group, arylalkyl group having a substituent or alkylsulfonyl group having 1 to 12 carbon atoms), $OR^{29}$ (wherein $R^{29}$ is acyl group having 1 to 12 carbon atoms, alkyl group having 1 to 12 carbon atoms, aryl group, aryl group having a substituent, arylalkyl group or arylalkyl group having a substituent), $—CO—R^{30}$ (wherein $R^{30}$ represents hydrogen atom, amino group, alkylamino group having 1 to 12 carbon atoms), alkyl group having 1 to 12 carbon atoms, aryl group, aryl group having a substituent, arylalkyl group, arylalkyl group having a substituent, aminosulfonyl group or alkylsulfinyl group having 1 to 12 carbon atoms;

$R^{1a}$, $R^{1b}$, $R^{1c}$, $R^{1d}$, $R^{1e}$ and $R^{1f}$ independently represent hydrogen atom, hydroxyl group, alkyl group having 1 to 12 carbon atoms, alkoxy group having 1 to 12 carbon atoms, aryl group, aryl group having a substituent, arylalkyl group or arylalkyl group having a substituent; $R^{20}$, $R^{21}$, $R^{22}$, $R^{23}$ and $R^{24}$ independently represent hydrogen atom, hydroxyl group, alkyl group having 1 to 12 carbon atoms, aryl group, aryl group having a substituent, arylalkyl group or arylalkyl group having a substituent;

a side chain consisting of $C^1—C^2—C^3—C^4—C^5—C^6$ may contain one or more double bonds;

$R^{25}$ represents hydroxyl group, OM (wherein M is alkaline metal atom, alkaline earth metal atom or $NH_4$), $NR^{26a}R^{26b}$ (wherein $R^{26a}$ and $R^{26b}$ independently represent hydrogen atom, acyl group having 1 to 12 carbon atoms, alkyl group having 1 to 12 carbon atoms, aryl group, aryl group having a substituent, arylalkyl group, arylalkyl group having a substituent or amino acid residue), $OR^{27}$ (wherein $R^{27}$ represents alkyl group having 1 to 12 carbon atoms, aryl group, aryl group having a substituent, arylalkyl group, arylalkyl group having a substituent or carbohydrate residue), alkyl group having 1 to 12 carbon atoms, aryl group, aryl group having a substituent, arylalkyl group or arylalkyl group having a substituent;

n is an integer of 1–7;

and in the above-mentioned five-membered ring, a double bond may be formed between the neighboring member carbon atoms], or represented by the general formula (XI):

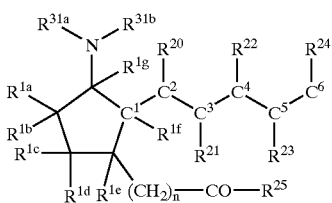

[wherein, $R^{1a}$, $R^{1b}$, $R^{1c}$, $R^{1d}$, $R^{1e}$, $R^{1f}$ and $R^{1g}$ independently represent hydrogen atom, hydroxyl group, alkyl group having 1 to 12 carbon atoms, alkoxy group having 1 to 12 carbon atoms, aryl group, aryl group having a substituent, arylalkyl group or arylalkyl group having a substituent; $R^{20}$, $R^{21}$, $R^{22}$, $R^{23}$ and $R^{24}$ independently represent hydrogen atom, hydroxyl group, alkyl group having 1 to 12 carbon atoms, aryl group, aryl group having a substituent, arylalkyl group or arylalkyl group having a substituent;

a side chain consisting of $C^1$—$C^2$—$C^3$—$C^4$—$C^5$—$C^6$ may contain one or more double bonds;

$R^{25}$ represents hydroxyl group, OM (wherein M represents alkaline metal atom, alkaline earth metal atom or $NH_4$), $NR^{26a}R^{26b}$ (wherein $R^{26a}$ and $R^{26b}$ independently represent hydrogen atom, acyl group having 1 to 12 carbon atoms, alkyl group having 1 to 12 carbon atoms, aryl group, aryl group having a substituent, arylalkyl group, arylalkyl group having a substituent or amino acid residue), $OR^{27}$ (wherein $R^{27}$ represents alkyl group having 1 to 12 carbon atoms, aryl group, aryl group having a substituent, arylalkyl group, arylalkyl group having a substituent or carbohydrate residue), alkyl group having 1 to 12 carbon atoms, aryl group, aryl group having a substituent, arylalkyl group or arylalkyl group having a substituent;

n is an integer of 1–7;

$R^{31a}$ and $R^{31b}$ independently represent hydrogen atom, hydroxyl group, acyl group having 1 to 12 carbon atoms, alkyl group having 1 to 12 carbon atoms, alkoxy group having 1 to 12 carbon atoms, aryl group, aryl group having a substituent, arylalkyl group, arylalkyl group having a substituent or amino acid residue;

and in the above-mentioned five-membered ring, a double bond may be formed between the neighboring member carbon atoms], then the taxane-type diterpene is recovered from the resulting cultures.

The taxane-type diterpene, which is an object of the method of the present invention, is not particularly limited to any diterpene as far as it has a taxane skeleton, and the illustrative examples include taxol, 10-deacetyltaxol, 7-epitaxol, baccatin III, 10-deacetylbaccatin III, 7-epibaccatin III, cephalomannine, 10-deacetylcephalomannine, 7-epicephalomannine, baccatin VI, taxane 1a, xylosylcephalomannine, xylosyltaxol, taxol C, 10-deacetyltaxol C, taxicin I, taxicin II, taxine I, taxine II, taxagifine and the like.

Examples of the plant to be used in the present invention which produces the taxane-type diterpene are those belonging to genus Taxus, such as *Taxus baccata* LINN, *Taxus cuspidata* SIEB. et ZUCC, *Taxus cuspidata* SIEB. et ZUCC var. nana REHDER, *Taxus brevifolia* NUTT, *Taxus canadensis* MARSH, *Taxus chinensis*, and *Taxus media*. Among these plants, *Taxus baccata* LINN and *Taxus media* are particularly preferable.

The tissue culture of the said plant is carried out by a conventionally known process except that the culture is carried out in the presence of coronatines, a bacterium which produces the coronatines, a culture solution or a culture extract of such bacterium, cyclic polysaccharides, fatty acids, or a compound represented by the above-mentioned general formulae (X) or (XI) according to the present invention.

Coronatines to be used in the present invention have been found as chlorosis inducing substance produced by Pseudomonas bacterium, and they have activities to induce necrosis of a plant, promotion of ethylene generation or aging of a plant. They also have an activity to promote the thickening growth of the tuber of potato, just like jasmonic acid.

As bacterium which produces coronatines, Pseudomonas bacteria and Xanthomonas bacteria have been known. Illustrative examples of Pseudomonas bacteria include *P. syringae* (IFO 3310), *P. glycinea*, *P. tabaci* (IFO 3508, IFO 14081), *P. aptata* (IFO 12655), *P. coronafaciens*, *P. phaseolicola* (IFO 12656, IFO 14078), *P. mori* (IFO 14053, IFO 14054, IFO 14055), *P. helianthi* (IFO 14077) and the like. Illustrative examples of Xanthomonas bacteria include *X. campestris* (IFO 13303, IFO 13551), *X. citri*, *X. cucurbitae* (IFO 13552), *X. phaseoli* (IFO 13553, IFO 13554), *X. pruni* (IFO 3780, IFO 13557) and the like.

Examples of coronatines include a compound represented by the general formula (I):

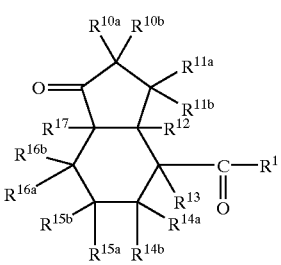

or general formula (II):

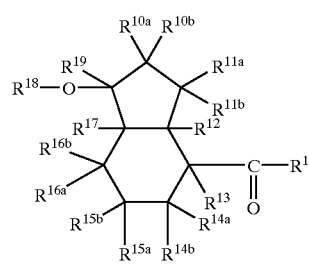

[wherein, $R^1$ represents hydroxyl group, $OR^2$ (wherein $R^2$ represents alkyl group having 1 to 6 carbon atoms or carbohydrate residue), $OM^1$ (wherein $M^1$ represents alkaline metal atom, alkaline earth metal atom or $NH_4$), or $NR^{3a}R^{3b}$ (wherein $R^{3a}$ and $R^{3b}$ represent independently hydrogen atom, acyl group having 1 to 6 carbon atoms, alkyl group having 1 to 6 carbon atoms, amino acid residue, or a group represented by the general formula (III):

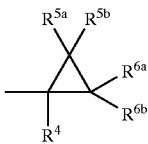
(III)

(wherein $R^4$ represents hydrogen atom, hydroxyl group, alkyl group having 1 to 6 carbon atoms, alkoxy group having 1 to 6 carbon atoms or a group represented by the following formula:

(wherein
$R^7$ represents hydroxyl group, $OM^2$ (wherein $M^2$ represents alkaline metal atom, alkaline earth metal atom or $NH_4$), $NR^{8a}R^{8b}$ (wherein $R^{8a}$ and $R^{8b}$ independently represent hydrogen atom, acyl group having 1 to 6 carbon atoms, alkyl group having 1 to 6 carbon atoms or amino acid residue), or $OR^9$ (wherein $R^9$ represents alkyl group having 1 to 6 carbon atoms or carbohydrate residue));
$R^{5a}$, $R^{5b}$, $R^{6a}$ and $R^{6b}$ independently represent hydrogen atom, hydroxyl group, alkyl group having 1 to 6 carbon atoms, or alkoxy group having 1 to 6 carbon atoms);
$R^{10a}$, $R^{10b}$, $R^{11a}$, $R^{11b}$, $R^{12}$, $R^{13}$, $R^{14a}$, $R^{14b}$, $R^{15a}$, $R^{15b}$, $R^{16a}$, $R^{16b}$, $R^{17}$ and $R^{19}$ independently represent hydrogen atom, hydroxyl group, alkyl group having 1 to 6 carbon atoms, or alkoxy group having 1 to 6 carbon atoms;
$R^{18}$ represents hydrogen atom, alkyl group having 1 to 6 carbon atoms, or carbohydrate residue;
a double bond may be formed between the neighboring member carbon atoms in the five-membered ring or six-membered ring in the formula].

In the above-mentioned general formulae (I), (II) and (III), illustrative examples of alkyl group having 1 to 6 carbon atoms represented by $R^2$, $R^{3a}$, $R^{3b}$, $R^4$, $R^{5a}$, $R^{5b}$, $R^{6a}$, $R^{6b}$, $R^{8a}$, $R^{8b}$, $R^9$, $R^{10a}$, $R^{10b}$, $R^{11a}$, $R^{11b}$, $R^{12}$, $R^{13}$, $R^{14a}$, $R^{14b}$, $R^{15a}$, $R^{15b}$, $R^{16a}$, $R^{16b}$, $R^{17}$, $R^{18}$ or $R^{19}$ include methyl, ethyl, n-propyl, isopropyl, n-butyl, isobutyl, sec-butyl, t-butyl, n-pentyl, neopentyl, t-pentyl, n-hexyl and isohexyl groups.

In the above-mentioned general formulae (I), (II) and (III), examples of alkoxy group having 1 to 6 carbon atoms represented by $R^4$, $R^{5a}$, $R^{5b}$, $R^{6a}$, $R^{6b}$, $R^{10a}$, $R^{10b}$, $R^{11a}$, $R^{11b}$, $R^{12}$, $R^{13}$, $R^{14a}$, $R^{14b}$, $R^{15a}$, $R^{15b}$, $R^{16a}$, $R^{16b}$, $R^{17}$ or $R^{19}$ include, for example, methoxy, ethoxy, n-propoxy, isopropoxy, n-butoxy, isobutoxy, sec-butoxy, t-butoxy, n-pentyloxy, neopentyloxy, t-pentyloxy, n-hexyloxy and isohexyloxy groups.

When $R^1$ or $R^7$ is $OM^1$ or $OM^2$, examples of the alkaline metal atom or alkaline earth metal atom represented by $M^1$ or $M^2$ include sodium, potassium and calcium.

When $R^1$ or $R^7$ is $NR^{3a}R^{3b}$ or $NR^{8a}R^{8b}$, the acyl group having 1 to 6 carbon atoms represented by $R^{3a}$, $R^{3b}$, $R^{8a}$ or $R^{8b}$ may have either a straight chain or a branched chain, and their examples include formyl, acetyl, propionyl, butyryl, valeryl, hexanoyl and acryloyl groups.

When $R^1$ or $R^7$ is $NR^{3a}R^{3b}$ or $NR^{8a}R^{8b}$, examples of the amino acid residue represented by $R^{3a}$, $R^{3b}$, $R^{8a}$ or $R^{8b}$ include isoleucyl, valyl, glutamyl and lysyl groups.

When $R^1$ or $R^7$ is $OR^2$ or $OR^9$, an example of the carbohydrate residue represented by $R^2$ or $R^9$ is glucopyranosyl group.

An example of the carbohydrate residue in the above-mentioned general formula (II) represented by $R^{18}$ includes glucopyranosyl group.

Preferable examples of the coronatines include coronatine (formula IV) and coronafacic acid (formula V).

Coronatine, which is a compound wherein coronafacic acid and 2-ethyl-1-aminocyclopropane-1-carboxylic acid are linked by amide bond, has the highest activity among those compounds represented by formula (I).

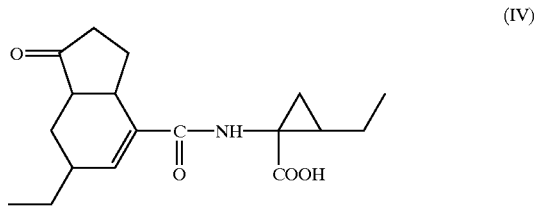
(IV)

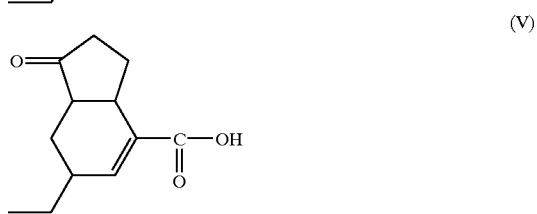
(V)

Coronatines to be used in the present invention have various stereoisomers (cis-trans isomers and optical isomers), and each isomer can be used alone or in the form of a mixture.

For adding coronatines, a bacterium which produces the coronatines, a culture solution or a culture extract of such bacteria to the culture medium, the concentration of the coronatines in the culture medium is normally required to be 0.001–1000 $\mu$M, and it is particularly preferable, according to the present invention, to control the concentration of the coronatines to be in the range of 0.01 to 100 $\mu$M.

By cultivating the cells and/or tissues of the above-mentioned plant by utilizing a culture medium which contains one or more substances selected from the group consisting of coronatines, a bacterium which produces the coronatines, a culture solution or a culture extract of such bacteria, according to the present invention, cultured cells and/or cultured tissues having higher taxane-type diterpene productivity can be obtained compared to the case wherein the substance was not added.

It has been reported that biosynthetic system involved in some secondary metabolism is activated by adding coronatines to plant cell cultures [W. Weiler et al., FEBS Letters 345:1 (1994)], however, there have been no reports on carrying out tissue culture of a plant producing a taxane-type diterpene in the presence of coronatines as a medium additive, and it has been beyond all expectations that the amount of the produced taxane-type diterpene was increased thereby.

A process to increase the productivity of taxane-type diterpene wherein a microorganism or a microorganism culture extract is used as elicitor for cultured cells of a plant belonging to genus Taxus is described in International Publication WO 93/17121 and U.S. Pat. No. 5019504. Though it is specified as elicitor in those publications, the degree of its effect is not given clearly. Besides there is no description regarding the bacteria belonging to genus Pseudomonas or genus Xanthomonas, which are the bacteria producing coronatines to be used in the present invention. Accordingly, it has been beyond all expectations that the amount of the produced taxane-type diterpene was increased by culturing cells of a plant belonging to genus Taxus in the presence of a bacterium which produces coronatines, or a culture solution or a culture extract of such bacteria.

The propagation of a bacetrium which produces coronatines is carried out with a propagation medium for general bacillus or a minimal medium.

An illustrative example of a culture solution of a bacterium which produces coronatines to be used in the present invention includes a culture solution treated by aseptic filtration after it is used for cultivating the bacteria.

Illustrative examples of a culture extract of a bacterium which produces coronatines to be used in the present invention include a culture solution which was autoclaved at 120° C. for 15 minutes after the bacteria had been cultured therein, or an extract of the culture solution of those bacteria which was extracted with an organic solvent such as ethyl acetate under acid conditions, which was optionally further refined with Sephadex LH 20 column and the like to give a partially refined fraction containing coronatine or coronafacic acid.

It is effective to add the coronatines, a bacterium which produces the coronatines, a culture solution or a culture extract of such bacterium, when the cultured cells are in the exponential growth phase through the stationary phase, and it is particularly preferable for the method of the present invention to add them in a transitional period from the exponential growth phase to the stationary phase. For example, when cells are transplanted in every 21 days, the 7th–16th day is the suitable time for addition of the coronatines, a bacterium which produces the coronatines, a culture solution or a culture extract of such bacterium. As for the addition, a predetermined amount of the substance can be added at a time, or they can be successively added in a plurality of parts.

An illustrative example of a cyclic polysaccharide to be used in the present invention includes cyclodextrin, cyclofructan and derivatives thereof.

The cyclic polysaccharide having a cavity inside due to its circular structure, the opening of the cavity and the exterior side showing hydrophilic property, and the interior side of the ring showing hydrophobic property, has clathrate activity to take an oil substance in the cavity. By utilizing this property, it has many uses such as changing a substance which is scarcely soluble in water to a water soluble substance, stabilizing an unstable substance, retaining a volatile substance such as a perfume, and controlling a peculiar odor. Commercially, it has been used for such food as freeze-dried tea, or ham and sausages for controlling the peculiar odor.

Cyclodextrin is a substance in which 6 to 8 glucose units are connected in the form of a donut, and is synthesized from starch by the function of cyclodextrin synthesizing enzyme which is produced by such special microorganism as *Bacillus macerans*. The cyclofructan is a substance in which 6 to 8 fructose units are connected in the form of a donut, and is synthesized from inulin by the function of cyclofructan synthesizing enzyme which is produced by such special microorganism as *Bacillus circulans*.

Examples of cyclodextrin and a derivative thereof, which are objects of the present invention, include α-cyclodextrin, βcyclodextrin, γ-cyclodextrin, or a branched dextrin thereof and a partially methylated dextrin thereof, and all of these can be utilized. Examples of the branched cyclodextrin include glycosyl-α-cyclodextrin, maltosyl-α-cyclodextrin, maltotriosyl-α-cyclodextrin, glycosyl-β-cyclodextrin, glycosyl-γ-cyclodextrin, galactosyl-α-cyclodextrin and the like, wherein a saccharide is bonded to the ring as a branch. As cyclofructan or a derivative thereof, a compound in which 6 to 8 fructose units are bonded by β2–1 fructoside bonds, a branched cyclofructan thereof, and partially methylated cyclofructan thereof can be utilized.

The concentration of the above-mentioned cyclic polysaccharides in a culture medium is preferably 0.01–50 mM, and it is more preferable, according to the present invention, to control the concentration of the cyclic polysaccharides to be in the range of 0.1 to 30 mM.

By carrying out the tissue culture of the cells and/or tissues of the above-mentioned plant by utilizing a culture medium to which cyclic polysaccharides are added according to the present invention, cultured cells or cultured tissues having higher taxane-type diterpene productivity can be obtained compared to the case wherein the substance was not added.

There have been no reports on carrying out tissue culture of a taxane-type diterpene producing plant in the presence of cyclic polysaccharides as a medium additive, and it has been beyond all expectations that the secretion of the taxane-type diterpene into the medium was promoted thereby, and the amount of the produced taxane-type diterpene was increased.

Particularly when the cyclic polysaccharide and other productivity improving substance (elicitor) are used together, the effect is heightened. Examples of such productivity improving substance include not only coronatines, a bacterium which produces the coronatines, a culture solution or a culture extract of such bacteria, fatty acids or a compound represented by the general formula (X) or general formula (XI) of the present invention, but also below-mentioned jasmonic acids, alkyl esters thereof, heavy metals, amines and antiethylene agents described in Japanese Patent Application No. 6-252528. It is also particularly effective to combine the use of the cyclic polysaccharides with the cultivation under the atmosphere of a low oxygen concentration described in Japanese Patent Application No. 6-146826.

Examples of fatty acids to be used in the present invention include a synthesized or natural fatty acid wherein the number of the carbon atoms in the main chain is 10–22, among them, the fatty acids having an even number of carbon atoms in its main chain are particularly preferable. These fatty acids can be saturated fatty acids or unsaturated fatty acids having one or more double bonds in its carbon chain. One or more hydrogen atoms bonded to the carbon chain may be substituted by hydrocarbon group having 1 to 6 carbon atoms, hydroxyl group, or amino group. The double bond to be contained in the above-mentioned unsaturated fatty acid can be either cis-form, trans-form or their mixture, however, a fatty acid containing the cis-form double bond is preferable.

Illustrative examples of the above-mentioned fatty acid include straight chain fatty acids such as capric acid, decenoic acid, lauric acid, dodecenoic acid, myristic acid, myristoleic acid, palmitic acid, palmitoleic acid, stearic acid, oleic acid, vaccenic acid, linolic acid, a-linolenic acid, y-linolenic acid, tetraoctadecenoic acid, arachic acid, arachidonic acid, eicosatetraenoic acid, eicosapentaenoic acid, behenic acid, and docosahexaenoic acid, hydroxy fatty acids such as ricinoleic acid, and branched fatty acids such as 14-methylpalmitic acid. Among these, oleic acid, linolic acid, linolenic acid and arachidonic acid are preferable, but particularly preferable is α-linolenic acid.

Among the substituents, examples of a hydrocarbon group having 1 to 6 carbon atoms include methyl, ethyl, propyl, cyclopropyl, butyl, isobutyl, pentyl and hexyl groups.

Among the substituents, examples of amino groups include amino, monomethylamino, and dimethylamino groups.

Fatty acids to be added to the culture medium may be a fatty acid derivative represented by the following general formula (XII):

$$R^{32}\text{—}COR^{33} \quad (XII)$$

[wherein $R^{32}$—CO represents an atomic group derived from the above-mentioned fatty acid;

$R^{33}$ represents $OR^{34}$ (wherein $R^{34}$ represents an alkyl group having 1 to 6 carbon atoms, or a carbohydrate residue), OM (wherein M represents alkaline metal atom, alkaline earth metal atom or $NH_4$), or $NR^{35a}R^{35b}$ (wherein $R^{35a}$ and $R^{35b}$ independently represent hydrogen atom, alkyl group having 1 to 6 carbon atoms, or amino acid residue)].

In the above-mentioned general formula (XII), examples of alkyl group having 1 to 6 carbon atoms represented by $R^{34}$, $R^{35a}$ and $R^{35b}$ include, methyl, ethyl, n-propyl, isopropyl, n-butyl, isobutyl, sec-butyl, t-butyl, n-pentyl, isopentyl, neopentyl, t-pentyl, n-hexyl, and isohexyl groups.

When $R^{33}$ is OM, examples of the alkaline metal atom or alkaline earth metal atom represented by M include, sodium, potassium and calcium.

When $R^{33}$ is $NR^{35a}R^{35b}$, examples of the amino acid residue represented by $R^{35a}$ or $R^{35b}$ include glycyl, leucyl, glutamyl, lysyl, phenylalanyl, isoleucyl, tyrosyl, and tryptophyl groups.

When $R^{33}$ is $OR^{34}$, an example of the carbohydrate residue represented by $R^{34}$ is glucopyranosyl group.

Fatty acids and/or a derivative thereof to be used in the present invention are preferably added to the culture medium to give the concentration of 0.01–1000 µM, and it is particularly preferable to control the concentration to be in the range of 0.1 to 500 µM from the view point of the effectiveness in improving the productivity of the taxane-type diterpene (when two or more kinds of fatty acids and/or derivatives are used in combination, the range of the concentration shown above represents the total concentration.)

According to the present invention, a natural oil containing a fatty acid or an enzymatic hydrolysate thereof can be used as well. Examples of a natural oil include vegetable oils such as rapeseed oil, soybean oil, linseed oil and safflower oil, and examples of the enzymatic hydrolysate include those of the above-mentioned vegetable oils decomposed by lipase. The concentration of the above-mentioned natural oil or the enzymatic hydrolysate thereof in the culture medium is preferably in the range of 1 to 1000 mg/l.

In addition to adding the fatty acids from outside of the system, it is also possible to add a lipid decomposing enzyme to the culture medium to partially hydrolyze the lipid such as glycerolipid constituting the said tissue and/or cell, so that the fatty acid is liberated into the medium. Examples of the lipid decomposing enzyme include lipase, phospholipase $A_1$, phospholipase $A_2$ and phospholipase B, and phospholipase $A_1$, phospholipase $A_2$ and phospholipase B having an optimal pH in an acid region are particularly preferable. According to the present invention, the preferable concentration of the above-mentioned enzyme to be added to the culture medium is 0.1–100 milligrams per liter of culture medium.

According to the present invention, the fatty acid, derivative thereof, natural oil, and lipid decomposing enzyme which satisfy the above-mentioned conditions can be used alone, or they can be combined randomly and used together.

These fatty acids or a derivative thereof, natural oil or lipid decomposing enzyme can be added to the culture medium from the initial stage of the cultivation or during the cultivation. It can be added altogether at any time during the cultivation, or they can be added in a plurality of parts.

Illustrative process of adding the above-mentioned fatty acids and natural oils to the culture medium include a process in which they are dissolved in an organic solvent such as ethanol and added, a process in which they are added together with a surfactant such as octyl-β-glucoside, or a process in which they are directly added to the culture medium followed by micelle formation which is carried out by supersonic wave treatment and the like. It is also possible that they are added directly to the medium and cultivation is carried out under the oil-water separated conditions.

Imino or amino derivatives of jasmonic acids to be used in the present invention are the compounds of the general formula (X) or (XI) respectively.

In the above-mentioned general formulae (X) or (XI), examples of the alkyl group having 1 to 12 carbon atoms represented by $R^{1a}$, $R^{1b}$, $R^{1c}$, $R^{1d}$, $R^{1e}$, $R^{1f}$, $R^{1g}$, $R^{20}$, $R^{21}$, $R^{22}$, $R^{23}$, $R^{24}$, $R^{25}$, $R^{28a}$, $R^{28b}$, $R^{29}$, $R^{26a}$, $R^{26b}$, $R^{27}$, $R^{31a}$, $R^{31b}$ or Y include methyl, ethyl, n-propyl, isopropyl, n-butyl, isobutyl, sec-butyl, t-butyl, n-pentyl, hexyl, heptyl, octyl, nonyl, decyl, undecyl, and dodecyl groups. The alkyl group having 3 or more carbon atoms includes a cyclic alkyl group such as cyclopropyl, cyclobutyl, cyclopentyl, and cyclohexyl groups.

In the above-mentioned general formulae (X) or (XI), examples of the alkoxy group having 1 to 12 carbon atoms represented by $R^{1a}$, $R^{1b}$, $R^{1c}$, $R^{1d}$, $R^{1e}$, $R^{1f}$, $R^{1g}$, $R^{31a}$ or $R^{31b}$ include methoxy, ethoxy, n-propoxy, isopropoxy, n-butoxy, isobutoxy, sec-butoxy, t-butoxy, pentyloxy, hexyloxy, heptyloxy, octyloxy, nonyloxy, decyloxy, undecyloxy and dodecyloxy groups. The alkoxy group having three or more carbon atoms includes an alkoxy group containing a cyclic alkyl group such as cyclopropyl, cyclobutyl, cyclopentyl and cyclohexyl groups.

In the above-mentioned general formulae (X) or (XI), the acyl group having 1 to 12 carbon atoms represented by $R^{28a}$, $R^{28b}$, $R^{26a}$, $R^{26b}$, $R^{29}$, $R^{31a}$ or $R^{31b}$ may have either a straight chain or a branched chain, or it can be an aromatic atomic group, and illustrative examples thereof include formyl, acetyl, propionyl, butyryl, valeryl, hexanoyl, acryloyl, capryloyl, pelargonyl, benzoyl, toluoyl, salicyloyl and cinnamoyl groups.

In the above-mentioned general formulae (X) or (XI), examples of the aryl group or aryl group having a substituent represented by $R^{1a}$, $R^{1b}$, $R^{1c}$, $R^{1d}$, $R^{1e}$, $R^{1f}$, $R^{1g}$, $R^{20}$, $R^{21}$, $R^{22}$, $R^{23}$, $R^{24}$, $R^{25}$, $R^{28a}$, $R^{28b}$, $R^{29}$, $R^{28b}$, $R^{29}$, $R^{26a}$, $R^{26b}$, $R^{27}$, $R^{27}$, $R^{31a}$, $R^{31a}$, $R^{31b}$ or Y include phenyl, p-methoxyphenyl, p-chlorophenyl, p-fluorophenyl and naphthyl groups.

In the above-mentioned general formulae (X) or (XI), examples of the arylalkyl group or arylalkyl group having a substituent represented by $R^{1a}$, $R^{1b}$, $R^{1}$, $R^{1d}$, $R^{1e}$, $R^{1f}$, $R^{1g}$, $R^{20}$, $R^{21}$, $R^{22}$, $R^{23}$, $R^{24}$, $R^{25}$, $R^{28a}$, $R^{28b}$, $R^{29}$, $R^{26a}$, $R^{26b}$, $R^{27}$, $R^{31a}$, $R^{31b}$ or Y include benzyl, p-methoxybenzyl, p-chlorobenzyl, and p-fluorobenzyl groups.

In the above-mentioned general formulae (X) or (XI), when $R^{25}$ is OM, examples of the alkaline metal atom or alkaline earth metal atom represented by M include sodium, potassium and calcium.

In the above-mentioned general formula (X), examples of the alkylsulfonyl group having 1 to 12 carbon atoms represented by $R^{28a}$ or $R^{28b}$ include methylsulfonyl, ethylsulfonyl, n-propylsulfonyl and isopropylsulfonyl groups.

In the above-mentioned general formula (X), when $R^{29}$ is —COR—$R^{30}$, examples of the alkylamino group having 1 to 12 carbon atoms represented by $R^{30}$ include methylamino, ethylamino, n-propylamino and isopropylamino groups.

In the above-mentioned general formula (X), examples of the alkylsulfinyl group having 1 to 12 carbon atoms represented by $R^{28a}$ or $R^{28b}$ include methylsulfinyl, ethylsulfinyl, n-propylsulfinyl and isopropylsulfinyl groups.

In the above-mentioned general formulae (X) or (XI), when $R^{25}$ is $NR^{26a}R^{26b}$, examples of the amino acid residue represented by $R^{26a}$ or $R^{26b}$ and examples of the amino acid residue represented by $R^{31a}$ or $R^{31b}$ in the general formula (XI) include isoleucyl, tyrosyl and tryptophyl groups.

In the above-mentioned general formulae (X) or (XI), when $R^{25}$ is $OR^{27}$, an example of the carbohydrate residue represented by $R^{27}$ is glucopyranosyl group.

In the compounds represented by the general formulae (X) or (XI), a double bond may be formed between the neighboring member carbon atoms in the five-membered ring.

Illustrative examples of the compound represented by the general formula (X) include those shown as follows;

(Compound A)
Y: —OH
$R^{1a}, R^{1b}, R^{1c}, R^{1d}, R^{1e}, R^{1f}, R^{20}, R^{21}, R^{22}, R^{23}, R^{24}$: H
A double bond is formed between $C^3$ and $C^4$.
$R^{25}$: —OCH$_3$
n: 1

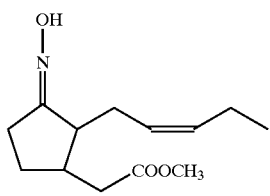

(Compound B)
Y: —OCH$_3$
$R^{1a}, R^{1b}, R^{1c}, R^{1d}, R^{1e}, R^{1f}, R^{20}, R^{21}, R^{22}, R^{23}, R^{24}$: H
A double bond is formed between $C^3$ and $C^4$.
$R^{25}$:—OCH$_3$
n: 1

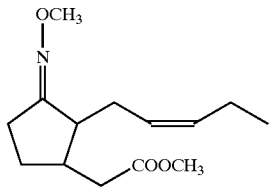

(Compound C)
Y: —NH$_2$
$R^{1a}, R^{1b}, R^{1c}, R^{1d}, R^{1e}, R^{1f}, R^{20}, R^{21}, R^{22}, R^{23}, R^{24}$: H
A double bond is formed between $C^3$ and $C^4$.
$R^{25}$:—OCH$_3$
n: 1

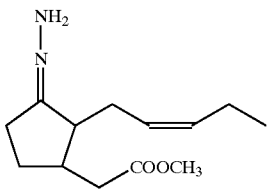

(Compound D)
Y: —NHCONH$_2$
$R^{1a}, R^{1b}, R^{1c}, R^{1d}, R^{1e}, R^{1f}, R^{20}, R^{21}, R^{22}, R^{23}, R^{24}$: H
A double bond is formed between $C^3$ and $C^4$.
$R^{25}$:—OCH$_3$
n: 1

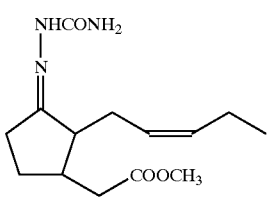

(Compound E)
Y:—NHCHO
$R^{1a}, R^{1b}, R^{1c}, R^{1d}, R^{1e}, R^{1f}, R^{20}, R^{21}, R^{22}, R^{23}, R^{24}$: H
A double bond is formed between $C^3$ and $C^4$.
$R^{25}$:—OCH$_3$
n=1

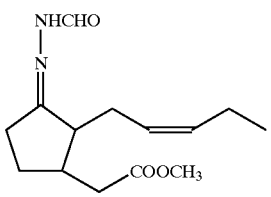

(Compound F)
Y:—NHSO$_2$CH$_3$
$R^{1a}, R^{1b}, R^{1c}, R^{1d}, R^{1e}, R^{1f}, R^{20}, R^{21}, R^{22}, R^{23}, R^{24}$: H
A double bond is formed between $C^3$ and $C^4$.
$R^{25}$:—OCH$_3$
n=1

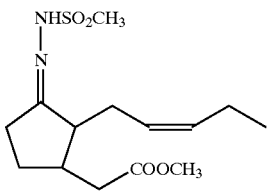

(Compound G)
Y:—CN
$R^{1a}, R^{1b}, R^{1c}, R^{1d}, R^{1e}, R^{1f}, R^{20}, R^{21}, R^{22}, R^{23}, R^{24}$: H A double bond is formed between $C^3$ and $C^4$.
$R^{25}$: —$OCH_3$
n=1

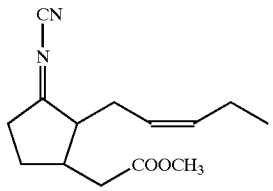

(Compound H)
Y: —$SO_2NH_2$
$R^{1a}$, $R^{1b}$, $R^{1c}$, $R^{1d}$, $R^{1e}$, $R^{1f}$, $R^{20}$, $R^{21}$, $R^{22}$, $R^{23}$, $R^{24}$: H
A double bond is formed between $C^3$ and $C^4$.
$R^{25}$: —$OCH_3$
n=1

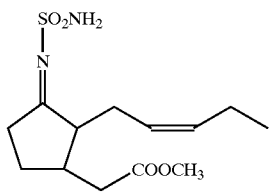

An illustrative example of the compound represented by the general formula (XI) is shown as follows;
(Compound I)
$R^{1a}$, $R^{1b}$, $R^{1c}$, $R^{1d}$, $R^{1e}$, $R^{1f}$, $R^{1g}$, $R^{20}$, $R^{21}$, $R^{22}$, $R^{23}$, $R^{24}$, $R^{31a}$: H
$R^{31b}$: OH
A double bond is formed between $C^3$ and $C^4$.
$R^{25}$: —$OCH_3$
n:1

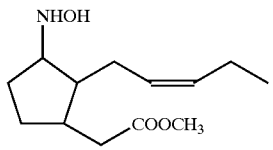

Compounds to be used in the present invention which are represented by the general formula (X) or (XI) have various stereoisomers, and each isomer can be used alone or the isomers can be used in the form of their mixture. Among the side chains of Compounds A to H, the isopentenyl group and the methoxycarbonylmethyl group are preferably in the cis-configuration.

The compound represented by the general formulae (X) or (XI) can be easily prepared by a process such as addition reaction of jasmonic acids with an ammonia derivative (for example, see "New Experimental Chemistry Course No.14, Synthesis and Reaction of Organic Compounds [III]" edited by The Chemical Society of Japan).

Illustrative examples of the ammonia derivative include hydroxylamine, phenylhydrazine, semicarbazide, O-methylhydroxylamine, O-ethylhydroxylamine, formic hydrazide, methanesulfonyl hydrazide and the like, or a salt thereof. When a salt is used, if necessary, a basic reagent can be liberated from the salt by adding sodium acetate or potassium acetate in the presence of a carbonyl derivative (jasmonic acids).

In the addition reaction, a basic nitrogen compound nucleophilically attacks the carbon in the carbonyl group, and it is preferable for the reaction solution to be controlled to have appropriate acidity.

The imino derivative of jasmonic acids obtained in such a way is further reacted with a complex hydrogen compound such as lithium aluminium hydride, sodium cyanoborohydride and sodium borohydride or a reducing agent such as borane to give an amino derivative of jasmonic acids.

The concentration of the compound represented by the general formulae (X) or (XI) in a culture medium is preferably 0.001–1000 $\mu$M, and it is more preferable to control the concentration to be in the range of 0.1 to 500 $\mu$M.

Promotion of the production of a specific secondary metabolite by addition of jasmonic acids to plant cell cultures is described in DE 4122208 however, there have been no reports on the production of the taxane-type diterpene. The present inventors have already found that the amount of the produced taxane-type diterpene in the resulting cultures can be increased by addition of jasmonic acids [Japanese Patent Application No. 6-104211, Japanese Patent Application No. 6-104212, Japanese Patent Application No. 7-47580], however, it has been beyond all expectations that imino or amino derivative of Jasmonic acids according to the present invention has higher production promoting effect than that of Jasmonic acids.

It is most effective to add the compound represented by the general formulae (X) or (XI) when the cultured cells are in the exponential growth phase or in the stationary phase, and it is particularly preferable for the method of the present invention to add the compound in a transitional period from the exponential growth phase to the stationary phase. For example, when cells are transplanted in every 21 days, the 7th–14th day is the suitable time for addition of the compound. The addition can be done at a time, or in a plurality of parts.

When a two-step culture is carried out by using a compound represented by the general formulae (X) or (XI), it is also possible that the cells are proliferated in a medium which is free from the compound, in the first culture step and the compound is added in the second culture step. The cells to be inoculated to the second culture step are preferably in the exponential growth phase or in the stationary phase.

According to the present invention, a cell or a tissue is cultured in a culture medium containing at least one substance selected from the group consisting of the above-mentioned coronatines, a bacterium which produces the coronatines, a culture solution or a culture extract of such bacteria, cyclic polysaccharides, fatty acids, and a compound represented by the general formulae (X) or (XI), then the taxane-type diterpene is recovered from the resulting cultures including cultured tissue, cultured cells and culture medium.

Examples of the medium to be used in the present invention include those known media which have been conventionally used for the plant tissue culture, such as medium of Murashige & Skoog (1962), medium of linsmaier Skoog (1965), Woody Plant Medium (1981), Gamborg's B-5 medium and Mitsui's M-9 medium.

A phytohormone, and if necessary a carbon source, an inorganic component, vitamins, amino acids and the like may be added as well to these media.

As the phytohormone, for example, auxins such as indoleacetic acid (IAA), naphthalenacetic acid (NAA), and 2,4-dichlorophenoxy acetic acid (2,4-D), and cytokinins such as kinetin, zeatin and dihydrozeatin can be used.

As the carbon source, a disaccharide such as sucrose, maltose and lactose, a monosaccharide such as glucose, fructose and galactose, starch or a mixture of two or more kinds of such sugar sources mixed at an appropriate ratio can be utilized.

Illustrative examples of the inorganic component include phosphorus, nitrogen, potassium, calcium, magnesium, sulfur, iron, manganese, zinc, boron, copper, molybdenum, chlorine, sodium, iodine and cobalt, and these components can be added in the form of such a compound as potassium nitrate, sodium nitrate, calcium nitrate, potassium chloride, potassium monohydrogenphosphate, potassium dihydrogenphosphate, calcium chloride, magnesium sulfate, sodium sulfate, ferrous sulfate, ferric sulfate, manganese sulfate, zinc sulfate, boric acid, copper sulfate, sodium molybdate, molybdenum trioxide, potassium iodide, cobalt chloride and the like.

Illustrative examples of the vitamins include biotin, thiamine (vitamin $B_1$), pyridoxine (vitamin $B_6$), pantothenic acid, inositol and nicotinic acid.

As the amino acids, for example, glycine, phenylalanine, leucine, glutamine, cysteine and the like can be added.

Generally, the phytohormones in a concentration of about 0.01–about 10 $\mu$M, the carbon source in a concentration of about 1–about 30 g/l, the inorganic component in a concentration of about 0.1 $\mu$–about 100 mM, and the vitamins and the amino acids respectively in a concentration of about 0.1–about 100 mg/l are used.

According to the present invention, both a liquid medium and such a solid medium that contains agar and gelan gum normally in an amount of 0.1–1% can be used, however, usually a liquid medium is preferable.

A piece of a tissue or a cell of a root, a growing point, a leaf, a stem, a seed, a pollen, an anther and a calyx and the like of the said plant, or cultured cells which are obtained by the tissue culture thereof with the above-mentioned medium or other conventional medium can be used for the tissue culture of the present invention.

The present invention can also be applied to neoplastic cell and/or hairy-root, obtained by infecting the plant tissue with *Agrobacterium tumefaciens* or *Agrobacterium rhizogenes*.

By carrying out the tissue culture of these tissues or cells in the presence of at least one substance selected from the group consisting of coronatines, a bacterium which produces the coronatines, a culture solution or a culture extract of such bacteria, cyclic polysaccharides, fatty acids, and a compound represented by the general formulae (X) or (XI), according to the present invention, cultured tissues or cultured cells having higher taxane-type diterpene productivity can be obtained compared to the case wherein the compound was not added, or no treatment was given.

Taxane-type diterpene can be separated from the cultures such as cultured tissues, cultured cells and culture medium, which are obtained according to the above-mentioned process, by extraction with an organic solvent such as methanol and dichloromethane. It is also possible to recover the taxane-type diterpene continuously by allowing an appropriate adsorbing agent or an organic solvent coexist in the culture medium.

One preferable example of the tissue culture according to the present invention can be illustrated as follows.

A piece of a plant body of a plant belonging to genus Taxus, such as a root, a growing point, a leaf, a stem, a seed and the like is sterilized and placed on Woody Plant Medium solidified with gelan gum, and kept at 10–35° C. for about 14–60 days so that a part of the tissue piece is changed to callus. By subculturing the callus thus obtained, the growing speed is gradually increased and stabilized callus can be obtained. By the stabilized callus, we refer to a callus which remains in callus state during cultivation without showing differentiation into a shoot or a root and the cells of which have uniform growing speed.

Such stabilized callus is inoculated to a liquid medium, suited for the proliferation, such as liquid Woody Plant Medium and proliferated. The growing speed is further increased in the liquid medium. According to the present invention, the stabilized callus or the cells constituting the above-mentioned callus are grown in a solid medium or a liquid medium containing at least one substance selected from the group consisting of coronatines, a bacterium which produces the coronatines, a culture solution or a culture extract of such bacteria, cyclic polysaccharides, fatty acids, and a compound represented by the general formulae (X) or (XI).

The culture temperature for the tissue culture according to the present invention is usually about 10–about 35° C., and preferably it is about 23–about 28° C. due to the high growing speed. As for the culture period, 14–42 days are preferable.

When a liquid medium is used for the culture according to the present invention, the cultured cells can be separated from the culture medium after the cultivation is completed, by such a method as decantation or filtration and the desired taxane-type diterpene can be separated from the cultured cells and/or the culture medium by such a method as extraction with an organic solvent.

The method of the present invention can be used together with a culture method to be carried out in the presence of jasmonic acids, which is disclosed as taxane-type compound production promoting substance in Japanese Patent Application No.7-47580, No. 6-104211, No. 6-104212, and No. 6-104213, to heighten the effect of the present invention.

Illustrative examples of jasmonic acids include jasmonic acid, a salt thereof, an alkyl ester thereof, cucurbic acid, a salt thereof, an alkyl ester thereof, tuberonic acid, a salt thereof and an alkyl ester thereof.

Among these, particularly preferable compounds can be exemplified by jasmonic acid, methyl jasmonate, tuberonic acid, methyl tuberonate, and cucurbic acid or methyl cucurbate from the view point of their high effectiveness in improving the productivity.

Jasmonic acids which can be used in the present invention include all the stereoisomers and the mixtures thereof.

The concentration of the jasmonic acids in a culture medium is 0.01–1000 $\mu$M, and it is particularly preferable to control the concentration of the jasmonic acids to be in the range of 0.1 to 500 $\mu$M.

It is effective to add jasmonic acids when the cultured cells are in the exponential growth phase or in the stationary phase, and it is particularly preferable to add jasmonic acids in a transitional period from the exponential growth phase to the stationary phase. The same can be said of the timing of the treatment for increasing the amount of the endogenous jasmonic acids to be produced. For example, when cells are transplanted in every 21 days, the 7th–16th day is the suitable time for addition of the jasmonic acids or the treatment to increase the amount of the endogenous jasmonic acids to be produced. The addition of the jasmonic acids or the treatment to increase the amount of the endogenous jasmonic acid to be produced can be done at a time, or in a plurality of parts.

Furthermore, the present invention can be used together with the method disclosed in Japanese Patent Application No.6-146826 wherein the culture is carried out by controlling the oxygen concentration in a gas phase in an culture vessel to less than the oxygen concentration in the atmosphere, from the initial stage of the culture, or by controlling the dissolved oxygen concentration in a fluid medium which is in contact with the tissue or the cell to less than the saturated dissolved oxygen concentration at that temperature from the initial stage of the culture.

Here, by the initial stage of the culture, we refer to from the time when the culture was started through the 7th day after the start of the culture, and the controlling of the oxygen concentration in the gas phase in the culture vessel or the controlling of the dissolved oxygen concentration in the fluid medium which is in contact with the tissue or the cell is preferably done from the beginning of the culture. The controlling period is not particularly limited, and the controlling under the said conditions can be done in the entire culture period, or only in a part of the entire culture period, however, it is preferable to carry out the control at least for 3 days during the entire culture period.

The oxygen concentration in the gas phase in the culture vessel is required to be controlled to 4–15%, and it is particularly preferable to control it to 6–12%. The dissolved oxygen concentration in the fluid medium is required to be controlled to 1–75% of the saturated dissolved oxygen concentration at that temperature and it is particularly preferable to control it to 10–75%.

The present invention can be also used together with the method disclosed in Japanese Patent Laid-Open Publication No.7-135967, Japanese Patent Application No.6-104213, wherein the cells are separated into a plurality of layers according to the difference in their specific gravities, and the cells contained in at least one layer are cultured.

The present invention can be also used together with the method disclosed in Japanese Patent Application No.6-201150, wherein the culture is carried out in the presence of at least one substance selected from the group consisting of compounds containing a heavy metal, complex ions containing a heavy metal and heavy metal ions.

As for the heavy metals, use of a copper group metal represented by silver or an iron group metal represented by cobalt is preferable. It is preferably used in the form of a compound containing the said heavy metal, a complex ion containing the said heavy metal or in the form of the said metal ion. Particularly preferable is silver thiosulfate ion. The concentration of the heavy metal is preferably $10^{-8}$ M–$10^{-2}$ M.

The present invention can be also used together with the method disclosed in Japanese Patent Application No.6-201151, wherein the culture is carried out in the presence of amines.

It is preferable to use at least one kind of amine selected from the group consisting of polyamines such as putrescine, spermidine, spermin, ethylene diamine, N,N-diethyl-1,3-propane diamine, diethylene triamine and a salt thereof. The concentration of the amine is preferably $10^{-8}$ M–$10^{-1}$ M.

It is also possible to combine the method of the present invention with two or more methods disclosed in the above-mentioned prior patents.

According to the present invention, a large amount of the taxane-type diterpene can be easily obtained by the tissue culture of a plant which produces the taxane-type diterpene using a tissue culture medium containing at least one kind of substance selected from the group consisting of coronatines, a bacterium which produces the coronatines, a culture solution or a culture extract of such bacteria, cyclic polysaccharides, fatty acids or an imino or amino derivative of jasmonic acids.

DESCRIPTION OF THE PREFERRED EMBODIMENTS

The invention will be further illustrated with the following examples, comparative examples, reference examples and synthesis examples, however, these examples are not to be construed to limit the scope of the invention.

EXAMPLE 1

A part of stem of *Taxus baccata* LINN which had been previously sterilized with 2% antiformin solution or 70% ethanol solution or the like, was placed on solid Woody Plant Medium (containing gelan gum of 0.25% by weight) to which naphthalenacetic acid had been added to give the concentration of $10^{-5}$M, and static culture was carried out at 25° C. in a dark place to provide callus of *Taxus baccata* LINN. One gram (fresh weight) of the callus was inoculated to an Erlenmeyer flask containing 20 ml of liquid Woody Plant Medium to which the above-mentioned component was added to give the same concentration and shake culture was carried out with a rotary shaker (amplification of 25 mm, 120 rpm) and the callus was subcultured in every 21 days to accelerate the growth rate thereof.

As the bacterium which produces coronatines, *Pseudomonas syringae* (IFO 3310) was cultured in a test tube containing 3 ml of bacterial culture medium 802 (Polypepton:1.0%, Yeast extract:0.2%, $MgSO_4.7H_2O$:0.1% , pH 7.0) at 180 rpm, 30° C. for 24 hours to proliferate the bacteria. Then 100 μl of the said culture solution containing the proliferated bacteria was inoculated to an Erlenmeyer flask containing 50 ml of glucose minimal medium (glucose:8.8 g/l, $KH_2PO_4$:2.6 g/l, $Na_2HPO_4.2H_2O$:6.9 g, $NH_4Cl$:2.5 g/l, $Na_2SO_4$:1 g/l, $FeSO_4$:0.01 g/l, $MnSO_4$:0.01 g/l, $MgCl_2$:0.05 g/l, pH 6.8) and further cultured at 30° C. for 24 hours. The culture solution of the bacterium which produces coronatines thus obtained was concentrated to about 1/20, then the pH was adjusted to pH 3 with 2N $H_2SO_4$ and extraction with ethyl acetate was carried out. The obtained carboxylic acid fraction was dried under reduced pressure, then dissolved in 2 ml of ethanol and the filtrate obtained by aseptic filtration thereof was used as the culture extract of the bacterium which produces coronatines.

One gram (fresh weight) of the cultured cells of *Taxus baccata* LINN thus obtained was inoculated to an Erlenmeyer flask containing 20 ml of liquid Woody Plant Medium, and shake culture was carried out at 25° C. for 14 days. On the 14th day after starting the culture, 50 μl of the culture extract of the bacterium which produces coronatines was added to the culture medium and the culture was further carried out for another 7 days.

After completing the culture, cultured cells of *Taxus baccata* LINN were harvested by filtration and lyophilized, then the dry weight was measured to obtain the yield of the cultured cells per liter of the liquid medium. Taxane-type diterpenes were extracted from the dried callus with methanol or the like, and they were determined by comparing with standard taxol, cephalomannine, and baccatin III using high performance liquid chromatography to measure the yields of the taxane-type diterpenes. The results are shown in Table 1.

Comparative Example 1

Example 1 was repeated except that the culture extract of the bacterium which produces coronatines was not added. The results are shown in Table 1.

EXAMPLE 2

Example 1 was repeated except that 1 ml of a filtrate obtained by aseptic filtration of cultures resulting from culture of *Pseudomonas syringae* in the minimal medium was added instead of the culture extract of the bacterium and culture was carried out. The results are shown in Table 1.

EXAMPLE 3

Example 1 was repeated except that 1 ml of a liquid obtained by autoclaving the cultures resulting from culture of *Pseudomonas syringae* in the minimal medium, was added inst

TABLE 2

|  | concentration of coronatines ($\mu$M) | yield of cultured cells (g/l) | yield*) of baccatin III (mg/l) | yield*) of taxol (mg/l) | yield*) of cephalomannine (mg/l) |
|---|---|---|---|---|---|
| Comparative Example 2 | 0 | 20.4 | 0.2 | 2.5 | 2.1 |
| Example 7 | 0.001 | 20.1 | 5.0 | 9.6 | 3.8 |
| Example 7 | 0.01 | 20.2 | 8.9 | 15.2 | 10.2 |
| Example 7 | 0.1 | 18.6 | 18.7 | 30.1 | 12.3 |
| Example 7 | 1 | 18.4 | 28.4 | 60.0 | 11.4 |
| Example 7 | 10 | 17.8 | 38.5 | 49.4 | 8.8 |
| Example 7 | 100 | 17.5 | 44.1 | 58.0 | 7.9 |
| Example 7 | 1000 | 15.0 | 13.2 | 23.1 | 6.5 |
| Example 8 | 1 | 18.1 | 25.0 | 51.1 | 9.2 |
| Example 9 | 1 | 19.5 | 4.6 | 11.3 | 6.6 |
| Example 10 | 10 | 18.6 | 12.4 | 6.2 | 3.0 |
| Example 11 | 10 | 19.2 | 8.4 | S.2 | 5.1 |
| Comparative Example 3 | 0 | 20.0 | 0.4 | 3.0 | 4.2 |
| Example 12 | 1 | 18.6 | 26.5 | 65.2 | 15.1 |

[*)The yield was calculated based on the total amount of production (in the cell + in the medium.]

EXAMPLE 13

A part of stem of *Taxus baccata* LINN which had been previously sterilized with 2% antiformin solution or 70% ethanol solution or the like, was placed on solid Woody Plant Medium (containing gelan gum of 0.25% by weight) to which naphthalenacetic acid had been added to give the concentration of $10^{-5}$ M, and static culture was carried out at 25° C. in a dark place to provide callus of *Taxus baccata* LINN. 0.1 g (fresh weight) of the callus was inoculated to a well having an inner diameter of 18 mm, containing 1 ml of liquid Woody Plant Medium to which the above-mentioned component was added to give the same concentration and shake culture was carried out with a rotary shaker (amplification of 25 mm, 120 rpm) and the callus was subcultured in every 28 days to accelerate the growth rate thereof.

One gram (fresh weight) of the cultured cells thus obtained was inoculated to an Erlenmeyer flask containing 20 ml of liquid Woody Plant Medium to which the above-mentioned component was added to give the same concentration, and shake culture was carried out at 25° C. for 14 days. On the 14th day after starting the culture, β-cyclodextrin was added to give the final concentration of 0.01 mM and the culture was further carried out for another 7 days.

After completing the culture, cultured cells of *Taxus baccata* LINN were harvested by filtration and lyophilized, then the dry weight was measured to obtain the yeild thereof per liter of the liquid medium. Taxane-type diterpenes were extracted from the dried callus with methanol or the like, and they were determined by comparing with standard taxol, cephalomannine, and baccatin III using high performance liquid chromatography to measure the yields of the taxane-type diterpenes. The results are shown in Table 3.

Comparative Example 4

Example 13 was repeated except that β-cyclodextrin was not added. The results are shown in Table 3.

EXAMPLE 14

Example 13 was repeated except that β-cyclodextrin was added to give the final concentration of 0.1 mM. The results are shown in Table 3.

EXAMPLE 15

Example 13 was repeated except that ,cyclodextrin was added to give the final concentration of 1 mM. The results are shown in Table 3.

EXAMPLE 16

Example 13 was repeated except that β-cyclodextrin was added to give the final concentration of 10 mM. The results are shown in Table 3.

EXAMPLE 17

Example 13 was repeated except that 6-0-β-D-glucosyl-βcyclodextrin was added instead of β-cyclodextrin to give the final concentration of 50 mM. The results are shown in Table 3.

EXAMPLES 18–22

Examples 13–17 were repeated except that further methyl ester of jasmonic acid was added to give the final concentration of 100 $\mu$M. The results are shown in Table 4.

Comparative Example 5

Comparative Example 4 was repeated except that further methyl ester of jasmonic acid was added to give the final concentration of 100 $\mu$M. The results are shown in Table 4.

EXAMPLE 23

Example 21 was repeated except that '-cyclodextrin was added instead of β-cyclodextrin to give the final concentration of 10 mM. The results are shown in Table 5.

EXAMPLE 24

Example 21 was repeated except that γ-cyclodextrin was added instead of β-cyclodextrin to give the final concentration of 10 mM. The results are shown in Table 5.

EXAMPLE 25

Example 21 was repeated except that cyclofructan (a compound in which 7 fructose units are connected) was added instead of β-cyclodextrin to give the final concentration of 10 mM. The results are shown in Table 5.

TABLE 3

|  | concentration of β-cyclodextrin (mM) | yeild of cultured cells (g/l) | yield*) of baccatin III (mg/l) | yield*) of taxol (mg/l) | yield*) of cephalomannine (mg/l) |
|---|---|---|---|---|---|
| Comparative Example 4 | 0 | 17.3 | 1.5 | 3.8 | 0.6 |
| Example 13 | 0.01 | 19.0 | 2.5 | 4.0 | 0.7 |
| Example 14 | 0.1 | 19.1 | 3.0 | 4.2 | 2.6 |
| Example 15 | 1 | 20.1 | 4.2 | 6.5 | 3.0 |
| Example 16 | 10 | 20.1 | 5.0 | 10.5 | 2.2 |
| Example 17 | 50**) | 20.5 | 3.5 | 8.2 | 1.3 |

TABLE 3-continued

| concentration of β-cyclo-dextrin (mM) | yeild of cultured cells (g/l) | yield*) of baccatin III (mg/l) | yield*) of taxol (mg/l) | yield*) of cephalo-mannine (mg/l) |
|---|---|---|---|---|

[*)The yield was calculated based on the total amount of production (in the cell + in the medium.)]
[**)6-O-α-D-glucosyl-β-cyclodextrin was used.]

TABLE 4

| | concentration of β-cyclo-dextrin (mM) | yield of cultured cells (g/l) | yield*) of baccatin III (mg/l) | yield*) of taxol (mg/l) | yield*) of cephalo-mannine (mg/l) |
|---|---|---|---|---|---|
| Comparative Example 5 | 0 | 15.4 | 49.7 | 25.9 | 7.3 |
| Example 18 | 0.01 | 15.6 | 54.6 | 28.5 | 8.0 |
| Example 19 | 0.1 | 16.3 | 62.6 | 35.4 | 9.6 |
| Lxample 20 | 1 | 15.4 | 76.0 | 42.3 | 10.1 |
| Example 21 | 10 | 17.3 | 54.2 | 64.4 | 12.5 |
| Example 22 | 50**) | 17.5 | 53.0 | 45.9 | 11.1 |

[*)The yield was calculated based on the total amount of production (in the cell + in the medium.)]
[**)6-O-α-D-glucosyl-β-cyclodextrin was used.]

TABLE 5

| | kind of cyclic poly-saccharides | yield of cultured cells (g/l) | yield*) of baccatin III (mg/l) | yield*) of taxol (mg/l) | yield*) of cephalo-mannine (mg/l) |
|---|---|---|---|---|---|
| Example 23 | α-cyclodextrin | 16.6 | 55.7 | 46.0 | 7.5 |
| Example 24 | γ-cyclodextrin | 17.5 | 85.2 | 45.2 | 8.5 |
| Example 25 | cyclofructan | 17.9 | 51.4 | 48.9 | 9.1 |

[*)The yield was calculated based on the total amount of production (in the cell + in the medium.)]

EXAMPLE 26

A part of stem of *Taxus baccata* LINN which had been previously sterilized with 2% antiformin solution or 70% ethanol solution or the like, was placed on solid Woody Plant Medium (containing gelan gum of 0.25% by weight) to which naphthalenacetic acid had been added to give the concentration of $10^{-5}$ M, and static culture was carried out at 25° C. in a dark place to provide callus of *Taxus baccata* LINN. One gram (fresh weight) of the callus was inoculated to an Erlenmeyer flask containing 20 ml of liquid Woody Plant Medium and shake culture was carried out with a rotary shaker (amplification of 25 mm, 100 rpm) and the callus was subcultured in every 21 days to accelerate the growth rate thereof.

Two grams (fresh weight) of the cultured cells thus obtained by liquid culture was inoculated to 20 ml of liquid Woody Plant Medium (contained in an Erlenmeyer flask of 100 ml) to which α-linolenic acid of 0.01–1000 μM (dissolved in ethanol) was added, and shake culture was carried out at 25° C. in a dark place with a rotary shaker (amplification of 25 mm, 100 rpm).

After completing the culture for 14 days, cultured cells were harvested by filtration and lyophilized, then the dry weight was measured to obtain the yield thereof. Taxane-type diterpenes were extracted from the dried callus and the culture medium with methanol or the like, and they were determined by comparing with standard taxol using high performance liquid chromatography to measure the yield of taxol. The results are shown in Table 6.

EXAMPLE 27

Example 26 was repeated except that oleic acid of 100 μM was added instead of α-linolenic acid. The results are shown in Table 7.

EXAMPLE 28

Example 26 was repeated except that linolic acid of 100 μM was added instead of α-linolenic acid. The results are shown in Table 7.

EXAMPLE 29

Example 26 was repeated except that arachidonic acid of 100 μM was added instead of a-linolenic acid. The results are shown in Table 7.

EXAMPLE 30

Example 26 was repeated except that rapeseed oil of 100 mg/l was added instead of α-linolenic acid. The results are shown in Table 7.

EXAMPLE 31

Example 26 was repeated except that species of the plant used was *Taxus media* (the part used for callus induction was seed). The results are shown in Table 8.

Comparative Example 6

Example 26 was repeated except that α-linolenic acid was not added. The results are shown in Table 6.

Comparative Example 7

Example 31 was repeated except that α-linolenic acid was not added. The results are shown in Table 8.

TABLE 6

| | concentration of | | yield of taxane-type diterpenes (mg/l) | | |
|---|---|---|---|---|---|
| | α-linolenic acid (μM) | yield of cells (g/l) | taxol | baccatin III | cephalo-mannine |
| Example 26 | 0.01 | 20 | 5 | 2 | 2 |
| Example 26 | 0.1 | 20 | 6 | 2 | 2 |
| Example 26 | 1 | 20 | 6 | 2 | 2 |
| Example 26 | 10 | 20 | 8 | 3 | 4 |
| Example 26 | 100 | 19 | 19 | 6 | 4 |
| Example 26 | 500 | 14 | 12 | 4 | 3 |
| Example 26 | 1000 | 12 | 7 | 2 | 2 |
| Comparative Example 6 | 0 | 20 | 4 | 1 | 1 |

TABLE 7

| | added fatty acids or natural oils | yield of cells (g/l) | yield of taxane-type diterpenes (mg/l) | | |
|---|---|---|---|---|---|
| | | | taxol | baccatin III | cephalo-mannine |
| Example 27 | oleic acid | 20 | 9 | 2 | 4 |
| Example 28 | linolic acid | 20 | 7 | 2 | 5 |

TABLE 7-continued

| | | yield of taxane-type diterpenes (mg/l) | | |
|---|---|---|---|---|
| added fatty acids or natural oils | yield of cells (g/l) | taxol | baccatin III | cephalo-mannine |
| Example 29 | arachidonic acid | 20 | 6 | 2 | 3 |
| Example 30 | rapeseed oil | 20 | 6 | 2 | 3 |
| Comparative Example 6 | none | 20 | 4 | 1 | 1 |

TABLE 8

| | yield of taxane-type diterpenes (mg/l) | | |
|---|---|---|---|
| yield of cells (g/l) | taxol | baccatin III | cephalo-mannine |
| Example 31 | 20 | 22 | 10 | 2 |
| Comparative Example 7 | 20 | 5 | 3 | 1 |

Synthesis Example 1

One gram (4.5 mmol) of methyl jasmonate was dissolved in 50 ml of methanol and cooled with ice, then 0.74 g (4.5 mmol) of hydroxylamine sulfate and 0.88 g (9.0 mmol) of potassium acetate were added thereto to carry out reaction. The reaction mixture was allowed to stand for one night and methanol was removed by evaporation, a saturated aqueous solution of sodium hydrogencarbonate was added and the resulting product was repeatedly extracted with ethyl acetate. The ethyl acetate extracts were collected, and water was removed with anhydrous sodium sulfate, then ethyl acetate was removed by drying under reduced pressure to give Compound A.

Compounds B–I were synthesized in a process analogous to that for Compound A except that the following reagents were employed instead of hydroxylamine sulfate.

| Compounds | Reagents |
|---|---|
| B | O-methylhydroxylamine hydrochloride |
| C | hydrazine hydrate |
| D | semicarbazide hydrochloride |
| E | formic hydrazide |
| F | methanesulfonyl hydrazide |
| G | cyanamide |
| H | sulfamide |

Synthesis Example 2

One gram of Compound A synthesized in Synthesis Example 1 was dissolved in 50 ml of methanol, and then a solution of 0.084 g (2.2 mmol) of sodium borohydride in 5 ml of methanol was dropped thereto. After completing of the dropping, the reaction mixture was further agitated for 30 minutes. The solution was concentrated until it became to about 10 ml. To the solution, a saturated solution of sodium hydrogencarbonate was added, and the product was repeatedly extracted with ethyl acetate. The ethyl acetate extracts were collected, and water was removed with anhydrous sodium sulfate, then ethyl acetate was removed by drying under reduced pressure to give Compound I.

EXAMPLE 32

A part of germ of *Taxus media* which had been previously sterilized with 2% antiformin solution or 70% ethanol solution or the like, was placed on solid Woody Plant Medium (containing gelan gum of 0.25% by weight) to which naphthalenacetic acid had been added to give the concentration of $10^{-5}$ M, and static culture was carried out at 25° C. in a dark place to provide callus of *Taxus media*. One gram (fresh weight) of the callus was inoculated to an Erlenmeyer flask containing 20 ml of liquid Woody Plant Medium to which above-mentioned component was added to give the same concentration, the and shake culture was carried out with a rotary shaker (amplification of 25 mm, 100 rpm) and the callus was subcultured in every 14 days to accelerate the growth rate thereof.

Two grams (fresh weight) of the cultured cells thus obtained was inoculated to an Erlenmeyer flask containing 20 ml of liquid Woody Plant Medium and Compound A was added as a derivative of jasmonic acids to give the final concentration of 0.01–1000 $\mu$M, and the culture was further carried out for another 14 days.

After completing the culture, cultured cells of *Taxus media* were harvested by filtration and lyophilized, then the dry weight was measured to obtain the yield of the cultured cells per liter of the liquid medium. Taxane-type diterpenes were extracted from the dried callus and the culture medium with methanol or the like, and they were determined by comparing with standard taxol, cephalomannine, and baccatin III using high performance liquid chromatography to measure the yields of the taxane-type diterpenes. The results are shown in Table 9.

Comparative Example 8

Example 32 was repeated except that a derivative of jasmonic acids was not added. The results are shown in Table 9.

Reference Example 1

Example 32 was repeated except that methyl jasmonate of 100 $\mu$M was added as a derivative of jasmonic acids. The results are shown in Table 9.

EXAMPLE 33

Example 32 was repeated except that Compound B of 100 $\mu$M was added as a derivative of jasmonic acids. The results are shown in Table 9.

EXAMPLE 34

Example 32 was repeated except that Compound C of 100 $\mu$M was added as a derivative of jasmonic acids. The results are shown in Table 9.

EXAMPLE 35

Example 32 was repeated except that Compound D of 100 $\mu$M was added as a derivative of jasmonic acids. The results are shown in Table 9.

EXAMPLE 36

Example 32 was repeated except that Compound E of 100 $\mu$M was added as a derivative of jasmonic acids. The results are shown in Table 9.

EXAMPLE 37

Example 32 was repeated except that Compound F of 100 $\mu$M was added as a derivative of jasmonic acids. The results are shown in Table 9.

EXAMPLE 38

Example 32 was repeated except that Compound G of 100 $\mu$M was added as a derivative of jasmonic acids. The results are shown in Table 9.

EXAMPLE 39

Example 32 was repeated except that Compound H of 100 $\mu$M was added as a derivative of jasmonic acids. The results are shown in Table 9.

EXAMPLE 40

Example 32 was repeated except that Compound I of 100 $\mu$M was added as a derivative of jasmonic acids. The results are shown in Table 9.

TABLE 9

|  | concentration of derivative of jasmonic acids ($\mu$M) | yield of cultured cells (g/l) | yield of taxane-type diterpenes (mg/l)* | | |
|---|---|---|---|---|---|
|  |  |  | baccatin III | taxol | cephalomannine |
| Comparative Example 8 | 0 | 22.2 | 5.2 | 14.2 | 2.1 |
| Reference Example 1 | 100 | 16.8 | 12.1 | 48.0 | 4.2 |
| Example 32 | 0.001 | 22.0 | 6.7 | 16.7 | 3.2 |
| Example 32 | 0.01 | 21.1 | 6.8 | 20.2 | 3.6 |
| Example 32 | 0.1 | 20.2 | 7.5 | 24.1 | 4.0 |
| Example 32 | 1 | 19.5 | 8.5 | 34.5 | 4.2 |
| Example 32 | 10 | 18.3 | 13.5 | 56.2 | 6.3 |
| Example 32 | 100 | 16.4 | 20.1 | 78.0 | 9.2 |
| Example 32 | 1000 | 14.0 | 9.3 | 17.2 | 3.5 |
| Example 33 | 100 | 16.1 | 18.0 | 65.3 | 5.2 |
| Example 34 | 100 | 16.7 | 16.5 | 55.0 | 6.6 |
| Example 35 | 100 | 15.3 | 17.2 | 56.3 | 5.0 |
| Example 36 | 100 | 17.2 | 18.5 | 79.5 | 6.2 |
| Example 37 | 100 | 17.1 | 15.3 | 73.3 | 5.9 |
| Example 38 | 100 | 14.3 | 14.5 | 82.9 | 5.0 |
| Example 39 | 100 | 17.1 | 19.0 | 85.0 | 7.5 |
| Example 40 | 100 | 16.2 | 14.2 | 73.3 | 5.5 |

[*) The yield was calculated based on the total amount of production (in the cell + in the medium.)]

What is claimed is:

1. A method of producing a taxane ring containing alkaloid compound wherein a cell and/or a tissue of a plant belonging to the genus Taxus, which produces the taxane ring containing alkaloid compound, is cultured in the presence of an effective taxane ring containing alkaloid compound producing amount of at least one substance selected from the group consisting of:

A) a compound in a concentration of 0.001 to 1000 $\mu$M of the formula X:

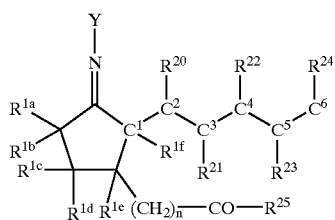

wherein

Y is:
i) a hydrogen atom,
ii) a hydroxyl group,
iii) a cyano group,
iv) $NR^{28a}R^{28b}$, wherein
   $R^{28a}$ and $R^{28b}$ independently are a hydrogen atom, carbamoyl group, acyl group having 1 to 12 carbon atoms, alkyl group having 1 to 12 carbon atoms, alkylsulfonyl group having 1 to 12 carbon atoms, aryl group, substituted aryl group, arylalkyl group or substituted arylalkyl group,
      wherein said aryl group or substituted aryl group is phenyl, p-methoxyphenyl, p-chlorophenyl, p-fluorophenyl or naphthyl, and wherein said arylalkyl group or substituted arylalkyl group is benzyl, p-methoxybenzyl, p-chlorobenzyl or p-fluorobenzyl,
$OR^{29}$,
   wherein $R^{29}$ is an acyl group having 1 to 12 carbon atoms, alkyl group having 1 to 12 carbon atoms, aryl group, substituted aryl group, arylalkyl group or substituted arylalkyl group,
      wherein said aryl group or substituted aryl group is phenyl, p-methoxyphenyl, p-chlorophenyl, p-fluorophenyl or naphthyl, and wherein said arylalkyl group or substituted arylalkyl group is benzyl, p-methoxybenzyl, p-chlorobenzyl or p-fluorobenzyl,
—CO—$R^{30}$,
   wherein $R^{30}$ is a hydrogen atom, amino group or alkylamino group having 1 to 12 carbon atoms; or
v) alkyl group having 1 to 12 carbon atoms, aminosulfonyl group, alkylsulfinyl group having 1 to 12 carbon atoms, aryl group, substituted aryl group, arylalkyl group or substituted arylalkyl group, wherein
   said aryl group or substituted aryl group is phenyl, p-methoxyphenyl, p-chlorophenyl, p-fluorophenyl or naphthyl, and wherein said arylalkyl group or substituted arylalkyl group is benzyl, p-methoxybenzyl, p-chlorobenzyl or p-fluorobenzyl;

$R^{1a}$, $R^{1b}$, $R^{1c}$, $R^{1d}$, $R^{1e}$ and $R^{1f}$ independently are a hydrogen atom; hydroxyl group; alkyl group having 1 to 12 carbon atoms; alkoxy group having 1 to 12 carbon atoms; aryl group; substituted aryl group; arylalkyl group; or substituted arylalkyl group,
   wherein said aryl group or substituted aryl group is phenyl, p-methoxyphenyl, p-chlorophenyl, p-fluorophenyl or naphthyl, and wherein said arylalkyl group or substituted arylalkyl group is benzyl, p-methoxybenzyl, p-chlorobenzyl or p-fluorobenzyl;

$R^{1a}$ and $R^{1c}$ optionally form a double bond or $R^{1c}$ and $R^{1e}$ optionally form a double bond or $R^{1e}$ and $R^{1f}$ optionally form a double bond;

$R^{20}$, $R^{21}$, $R^{22}$, $R^{23}$ and $R^{24}$ independently are a hydrogen atom; hydroxyl group; alkyl group having 1 to 12 carbon atoms; aryl group; substituted aryl group; arylalkyl group or substituted arylalkyl group,
   wherein said aryl group or substituted aryl group is phenyl, p-methoxyphenyl, p-chlorophenyl, p-fluorophenyl or naphthyl, and
   wherein said arylalkyl group or substituted arylalkyl group is benzyl, p-methoxybenzyl, p-chlorobenzyl or p-fluorobenzyl;

a side chain consisting of $C^1$—$C^2$—$C^3$—$C^4$—$C^5$—$C^6$ which has one or more double bonds;

$R^{25}$ is:
  i) a hydroxyl group,
  ii) OM, wherein M is an alkaline metal atom, alkaline earth metal atom or $NH_4$,
  iii) $NR^{26a}R^{26b}$, wherein $R^{26a}$ and $R^{26b}$ independently are a hydrogen atom, acyl group having 1 to 12 carbon atoms, alkyl group having 1 to 12 carbon atoms, amino acid residue, aryl group, substituted aryl group, arylalkyl group or substituted arylalkyl group,
    wherein said aryl group or substituted aryl group is phenyl, p-methoxyphenyl, p-chlorophenyl, p-fluorophenyl or naphthyl, and
    wherein said arylalkyl group or substituted arylalkyl group is benzyl, p-methoxybenzyl, p-chlorobenzyl or p-fluorobenzyl;
  iv) $OR^{27}$, wherein $R^{27}$ is an alkyl group having 1 to 12 carbon atoms, carbohydrate residue, aryl group, substituted aryl group, arylalkyl group or substituted arylalkyl group,
    wherein said aryl group or substituted aryl group is phenyl, p-methoxyphenyl, p-chlorophenyl, p-fluorophenyl or naphthyl, and
    wherein said arylalkyl group or substituted arylalkyl group is benzyl, p-methoxybenzyl, p-chlorobenzyl or p-fluorobenzyl; or
  v) an alkyl group having 1 to 12 carbon atoms, aryl group, substituted aryl group, arylalkyl group or substituted arylalkyl group,
    wherein said aryl group or substituted aryl group is phenyl, p-methoxyphenyl, p-chlorophenyl, p-fluorophenyl or naphthyl, and
    wherein said arylalkyl group or substituted arylalkyl group is benzyl, p-methoxybenzyl, p-chlorobenzyl or p-fluorobenzyl;

n is an integer of 1–7; and

B) a compound in a concentration of 0.001 to 1000 μM of the formula XI:

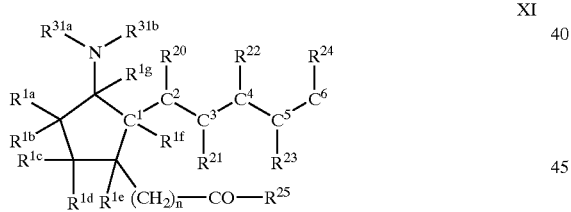

XI wherein $R^{1a}$, $R^{1b}$, $R^{1c}$, $R^{1d}$, $R^{1e}$, $R^{1f}$ and $R^{1g}$ independently are a hydrogen atom; hydroxyl group; alkyl group having 1 to 12 carbon atoms; alkoxy group having 1 to 12 carbon atoms; aryl group; substituted aryl group; arylalkyl group; or substituted arylalkyl group,
  wherein said aryl group or substituted aryl group is phenyl, p-methoxyphenyl, p-chlorophenyl, p-fluorophenyl or naphthyl, and
  wherein said arylalkyl group or substituted arylalkyl group is benzyl, p-methoxybenzyl, p-chlorobenzyl or p-fluorobenzyl;

$R^{1a}$ and $R^{1c}$ optionally form a double bond or $R^{1c}$ and $R^{1e}$ optionally form a double bond or $R^{1e}$ and $R^{1f}$ optionally form a double bond or $R^{1f}$ and $R^{1g}$ optionally form a double bond or $R^{1a}$ and $R^{1g}$ optionally form a double bond;

$R^{20}$, $R^{21}$, $R^{22}$, $R^{23}$ and $R^{24}$ independently are a hydrogen atom; hydroxyl group; alkyl group having 1 to 12 carbon atoms; aryl group; substituted aryl group; arylalkyl group or substituted arylalkyl group,
  wherein said aryl group or substituted aryl group is phenyl, p-methoxyphenyl, p-chlorophenyl, p-fluorophenyl or naphthyl, and
  wherein said arylalkyl group or substituted arylalkyl group is benzyl, p-methoxybenzyl, p-chlorobenzyl or p-fluorobenzyl;

a side chain consisting of $C^1$—$C^2$—$C^3$—$C^4$—$C^5$—$C^6$ which has one or more double bonds;

$R^{25}$ is:
  i) a hydroxyl group,
  ii) OM, wherein M is an alkaline metal atom, alkaline earth metal atom or $NH_4$,
  iii) $NR^{26a}R^{26b}$, wherein $R^{26a}$ and $R^{26b}$ independently are a hydrogen atom, acyl group having 1 to 12 carbon atoms, alkyl group having 1 to 12 carbon atoms, amino acid residue, aryl group, substituted aryl group, arylalkyl group or substituted arylalkyl group,
    wherein said aryl group or substituted aryl group is phenyl, p-methoxyphenyl, p-chlorophenyl, p-fluorophenyl or naphthyl and
    wherein said arylalkyl group or substituted arylalkyl group is benzyl, p-methoxybenzyl, p-chlorobenzyl or p-fluorobenzyl;
  iv) $OR^{27}$, wherein $R^{27}$ is an alkyl group having 1 to 12 carbon atoms, carbohydrate residue, aryl group, substituted aryl group, arylalkyl group or substituted arylalkyl group,
    wherein said aryl group or substituted aryl group is phenyl, p-methoxyphenyl, p-chlorophenyl, p-fluorophenyl or naphthyl, and
    wherein said arylalkyl group or substituted arylalkyl group is benzyl, p-methoxybenzyl, p-chlorobenzyl or p-fluorobenzyl;
  v) alkyl group having 1 to 12 carbon atoms, aryl group, substituted aryl group, arylalkyl group or substituted arylalkyl group,
    wherein said aryl group or substituted aryl group is phenyl, p-methoxyphenyl, p-chlorophenyl, p-fluorophenyl or naphthyl, and
    wherein said arylalkyl group or substituted arylalkyl group is benzyl, p-methoxybenzyl, p-chlorobenzyl or p-fluorobenzyl;

$R^{31a}$ and $R^{31b}$ independently are a hydrogen atom; hydroxyl group; acyl group having 1 to 12 carbon atoms; alkyl group having 1 to 12 carbon atoms; alkoxy group having 1 to 12 carbon atoms; amino acid residue; aryl group; substituted aryl group; arylalkyl group; or substituted arylalkyl group,
  wherein said aryl group or substituted aryl group is phenyl, p-methoxyphenyl, p-chlorophenyl, p-fluorophenyl or naphthyl, and
  wherein said arylalkyl group or substituted arylalkyl group is benzyl, p-methoxybenzyl, p-chlorobenzyl or p-fluorobenzyl;

then the taxane ring containing alkaloid compound is recovered from resulting cultures of the cell and/or tissue of a plant.

2. A method according to claim 1, wherein the taxane ring containing alkaloid compound is at least one substance selected from the group consisting of taxol, 10-deacetyltaxol, 7-epitaxol, baccatin III, 10-deacetylbaccatin III, 7-epibaccatin III, cephalomannine, 10-deacetylcephalomannine, 7-epicephalomannine, baccatin VI, taxane 1a, xylosylcephalomannine, xylosyltaxol, taxol C, 10-deacetyltaxol C, taxicin I, taxicin II, taxine I, taxine II and taxagifine.

3. A method according to claim 1, wherein the plant which produces the taxane ring containing alkaloid compound is *Taxus baccata* or *Taxus media*.

* * * * *